United States Patent
Wachter et al.

(10) Patent No.: US 6,964,775 B1
(45) Date of Patent: *Nov. 15, 2005

(54) DECORATIVE COSMETIC PREPARATIONS

(75) Inventors: Rolf Wachter, Dusseldorf (DE); Ute Griesbach, Dusseldorf (DE); Achim Ansmann, Erkrath (DE); Bernd Fabry, Korschenbroich (DE); Rolf E. Engstad, Tromso (NO)

(73) Assignee: Biotec ASA, Tromso (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/958,056

(22) PCT Filed: Apr. 11, 2000

(86) PCT No.: PCT/EP00/03193

§ 371 (c)(1),
(2), (4) Date: Jan. 7, 2002

(87) PCT Pub. No.: WO00/62754

PCT Pub. Date: Oct. 26, 2000

(30) Foreign Application Priority Data

Apr. 20, 1999 (DE) ................ 199 17 744

(51) Int. Cl.[7] .......................................... A61K 7/001

(52) U.S. Cl. ................ 424/401; 424/400; 424/495.16; 514/195.16

(58) Field of Search ................ 424/400, 401, 424/495.16; 514/54

(56) References Cited

U.S. PATENT DOCUMENTS

| 3,659,025 A | 4/1972 | Halleck |
| 5,158,772 A | 10/1992 | Davis |
| 5,223,491 A | 6/1993 | Donzis |
| 5,385,832 A | 1/1995 | Tuse et al. |
| 5,653,967 A | 8/1997 | Murphy |

FOREIGN PATENT DOCUMENTS

| JP | 3167102 | 7/1991 |
| WO | WO 95/30022 | * 11/1995 |
| WO | WO 96/28476 | * 9/1996 |
| WO | WO 9628476 | 9/1996 |

* cited by examiner

Primary Examiner—Gary Kunz
Assistant Examiner—Konata M. George
(74) Attorney, Agent, or Firm—Ladas & Parry LLP

(57) ABSTRACT

Decorative cosmetic preparations that contain water-soluble β-(1,3) glucans, which have intact β-(1,3) side-chains and are free from repetitive β-(1,6) linkages and a method of producing the same are disclosed.

12 Claims, No Drawings

DECORATIVE COSMETIC PREPARATIONS

FIELD OF THE INVENTION

The invention belongs to the field of decorative cosmetics and concerns preparations which contain selected polysaccarides of the type β-(1,3) glucans.

PRIOR ART

The formation of wrinkles is induced through the degradation of different macro molecules such as for example elastin and collagen, which are responsible for the elastases. Many inflammatory skin diseases, such as for example psoriasis or UV erythema, can also causatively be linked to an increased concentration of serine proteases, such as e.g. elastase in the upper skin areas [see R. Voegeli et al. in *Cosm. Toil.* 111, 51(1996)].

The formation of wrinkles i the skin is normally not counteracted by means of physiological active principles, but by means of cosmetic agents. In addition to pure "anti-ageing products", a lot of decorative cosmetic products also have been established in the market, which in addition have a healing and protecting effect. Usually these are liposomes loaded with water or aqueous active agents, which through the fat layer of the skin are reaching the epidermis, where they gradually dissolve and through continuous water release compensate the skin recesses and regulate the moisture content of the skin. However, this effect is no combat against the causes, but only has a so-called "repair effect", which only lasts for a short period of time.

The use of specific polysaccharides as agents against the skin ageing is known from prior art. Thus it has e.g. been suggested in the patent U.S. Pat. No. 5,223,491 to employ a carboxymethylated β-1,3 glucan, which has been extracted from the yeast fungus *Saccharomyces cerevisiae*, for topical application. The glucan is, however, insoluble in water and can accordingly only be formulated with great difficulties. From the teachings in the two papers DE-A1 3744345 (Lomapham) and EP-B1 0175667 (Lam) are glucans well suited for stimulation of the activity of the macrophages. The pharmaceutical effect of different glucans is further known from the two European patent applications EP-A1 045338 (Debat) and EP-A1 0561408 (Kaken). Object of the European patent EP-B1 0500718 (Donzis) is the use of water insoluble β-(1,3) glucans, which are obtained from the cell walls of yeast, for revitalization of the skin. The complex task task of the present invention was therefore to make available decorative cosmetic preparations, such as e.g. make-ups, lid shades, etc. which in addition to the accentuating colour effect demanded by the user, should feature a preventative effect against the loss of moisture and the formation of wrinkles, and at the same time a nursing and immunestimulating effect.

DESCRIPTION OF THE INVENTION

The object of the invention are decorative cosmetic preparations, containing water soluble β-(1,3) glucans, which are substantially free from β-(1,6) linkages. Surprisingly it was found, that decorative cosmetic preparations which according to the invention contain the specific glucans, in relation to the products according to the state of the art show an improved maintenance effect. At the same time the binding of moisture is improved, the formation of wrinkles is counteracted and the immune system is stimulated. Decorative cosmetic preparations in this connection is meant to be tinting face cremes, make-up rouges, face powder, lid shades, kohls, mascaras, eye liners, lipsticks, cover sticks, nail polishes and suchlike.

Water Soluble β-(1,3) Glucans

The term glucans means homopolysaccharides based on glucose. Depending on sterical linking there is a difference between β-(1,3), β-(1,4) and β-( 1,6) glucans. β-(1,3) Glucans normally show a helical structure, whereas glucans with a (1,4) linkage generally have a linear structure. The β-glucans of the invention have a (1,3) structure, i.e. they are substantillay free from undesired (1,6) linkages. Preferably such β-(1,3) glucans are used where the side chains exclusively show (1,3) linkages. Especially the agents contain glucans which are obtained on the basis of yeasts from the family *Saccaomyces*, especially *Saccharomyces cerevisiae*. Glucans of this type are available in technical amounts according to known methods. The international patent application WO 95/30022 (Biotec-Mackzymal) describes a method for producing such substances, wherein glucans with β-(1,3) and β-(1,6) linkages are brought in contact with β-(1,6) glucanases in such a way, that practically all β-(1,6) linkages are loosened. Preferably used for the manufacture of these glucans are glucanases based on *Trichodermia harzianum*. As to the manufacture and availability of the glucans contained in these agents, reference is made to the above cited publication. The glucans can be contained in the preparations in amounts of 0.1 to 5, preferably 0.2 to 5, and especially 0.5 to 1% by weight, based on the agents.

COMMERCIAL APPLICABILITY

The preparations according to the invention may further contain as additional auxiliary and additional agents oil bodies, emulsifiers, hyperfatting agents, consistency substances, thickening agents, polymers, silicone compounds, fats, waxes, stabilizing agents, biogenic active substances, deodorants, swelling agents, UV light protection agents, antioxidants, organic and inorganic colour pigments, hydrotropes, preservatives, solubilizing agents, perfume oils, colouring agents and suchlike. The preparations can be free from water or practically free from water (e.g. face powder or nail polish); they can, however, contain high amounts of water as a further auxiliary agent (e.g. creme preparations). Preferably the preparations according to the invention contain (a) 0.1 to 1% by weight of water soluble β-(1,3) glucans, which are substantially free from β-(1,6) linkages, and
(b) 99 to 99.9% by weight of auxiliary and additional substances.

As oil bodies use can be made of for example Guerbet alcohols based on fatty alcohols with 6 to 18, preferably 8 to 10 carbon atoms, esters of linear $C_6$–$C_{22}$ fatty acids with linear $C_6$–$C_{22}$ fatty alcohols, esters of branched $C_6$–$C_{13}$ carboxylic acids with linear $C_6$–$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition esters of linear $C_6$–$C_{22}$ fatty acids with branched alcohols, especially 2-ethylhexanol, esters of hydroxycarboxylic acids with linear or branched $C_6$–$C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6$–$C_{10}$ fatty acids, liquid mixtures of mono-/di-/triglycerides based on $C_6$–$C_{18}$ fatty acids, esters of $C_6$–$C_{22}$ fatty alcohols and/or Guerbet alcohols with aromatic carboxylic acids, especially benzoic acid, esters of $C_2$–$C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolv® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used As emulsifiers for example nonionic surfactants from at least one of the following groups may be used:
(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;
(2) $C_{12/18}$ fatty acid mono- and diesters of addition products of 1 to 30 moles ethylene oxide and glycerol;
(3) glycerol mono- and diesters and sorbitan mono- and diesters of saturated and unsaturated fatty acids with 6 to 22 carbon atoms and their ethylene oxide addition products;
(4) alkyl mono- and oligoglycosides with 8 to 22 carbon atoms in the alkyl group and their ethoxylated analogues;
(5) addition products of 15 to 60 moles ethylene oxide on *ricinus* oil and/or hardened *ricinus* oil;
(6) polyol and especially polyglycerol esters, such as e.g. polyglycerol polyricinoleate, polyglycerol poly-12-hydroxy stearate or polyglycerol dimerate isostearate, and also mixtures of compounds from more of these classes of substances;
(7) addition products of 2 to 15 moles ethylene oxide on *ricinus* oil and/or hardened *ricinus* oil;
(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);
(9) mono-, di- and trialkylphosphates as well as mono-, di- and/or tri-PEG alkylphosphates and their salts;
(10) wool wax alcohols;
(11) polysiloxane/polyalkyl/polyether copolymers or corresponding derivatives;
(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,
(13) polyalkylene glycols, as well as
(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on *ricinus* oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{12/18}$ fatty acid mono- and diesters of addition products of ethylene oxide on glycerol are known from DE 2024051 PS as revertive fatting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologous which is usual for such products of technical quality.

Zwitterionic surfactants can also be used as emulsifiers. The term zwitterionic surfactants is intended to mean such surface active compounds which in their molecule have at least a quaternary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylaminopropyl-N,N-dimethyl ammonium glycinate, for example the coco acylaminopropyl dimethyl ammonium glycinate, and 2-alkyl-3-carboxylmethyl hydroxyethyl imidazoline with in each case 8 to 18 C atoms in the alkyl or acyl groups, as well as the coco acylaminoethyl hydroxyethyl carboxymethyl glycinate. Especially preferred is that under the CTFA term *cocamidopropyl betaine* known fatty acid amide derivative.

Also suitable emulsifiers are ampholytic surfactants. Ampholytic surfactants are such surface active compounds which in addition to a $C_{8/18}$ alkyl or acyl group in the molecule at least contain a free amino group and at least one —COOH or —$SO_3H$ group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylamino propionate and the $C_{12/18}$ acylsarcosine. In addition to the ampholytic, also quaternary emulsifiers can be used, of which ester salts of the type of esterquats, preferably methylquaternised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As consistency givers preferably use is made of fatty alcohols or hydroxy fatty alcohols with 12 to 22 carbon atoms and preferably 16 to 18 carbon atoms and additionally partial glycerides, fatty acids or hydroxy fatty acids. A combination of these substances with alkyl oligoglucosides and/or fatty acid-N-methyl glucamides with the same chain length and/ or polyglycerol-poly-12-hydroxy stearates is preferred.

Suitable thickening agents are for example types of aerosil (hydrophilic silicic acids), polysaccharides, especially xanthan gum, guar—guar, agar—agar, alginates and methyl celluloses, carboxymethyl celluloses and hydroxyethyl cellulose, as well as higher molecular polyethylene glycol mono- and diesters of fatty acids, polyacrylates, (e.g. Carbopols® from Goodrich or Synthalenes® from Sigma), polyacrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as elektrolytes such as sodium chloride and ammonium chloride.

Suitable cationic polymers are for example cationic cellulose derivatives, such as e.g. a quaternized hydroxyethyl cellulose, which is available under the name of Polymer JR 400® from Amerchol, cationic starch, copolymers of diallyl ammonium salts and acrylamides, quaternized vinylpyrrolidone/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequat®L/Grünau), quaternized wheat polypeptides, polyethylene imine, cationic silicone polymers, such as e.g. amidomethicones, copolymers of adipic acid and dimethylamino hydroxypropyl diethylenetriamine (Cartaretine®/ Sandoz), copolymers of acrylic acid with dimethyl diallylammonium chloride (Merquat® 550/Chemviron), polyamino polyamides, such as e.g. described in FR 2252840 A, as well as their cross-linked water soluble polymers, cationic chitin derivatives such as for example quaternized chitosan, possibly microcrystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quaternised ammonium salt polymers, such as e.g. Mirapol® A-15, Mirapol® AD-1, Mirapol® AZ-1 from Miranol.

As exemplary anionic, zwitterionic, amphoteric and nonionic polymers the following can be used: Vinyl acetate/ crotonic acid copolymers, vinyl pyrrolidone/vinyl acrylate copolymers, vinyl acetate/butyl maleate/isobornyl acrylate copolymers, methyl vinylether/maleic acid anhydride copolymers and their esters, non-cross-linked and with polyols cross-linked polyacrylic acids, acrylamido propyltrimethyl ammonium chloride/acrylate copolymers, octylacrylamide/methyl methacrylate/tert.-butylaminoethyl methacrylate/2-hydroxypropyl methacrylate copolymers, polyvinylpyrrolidone, vinylpyrrolidone/vinylacetate copolymers, vinylpyrrolidone/dimethylamino ethylmethacrylate/vinyl caprolactam terpolymers as well as possibly derivatized cellulose ethers and silicones.

Suitable silicon compounds are for example dimethyl polysiloxane, methylphenyl polysiloxane, cyclic silicones as well as amino, fatty acid, alcohol, polyether, epoxy, fluorine, glykoside and/or alkyl modified silicone compounds, which at room temperature can be in the liquid as well as in the resin state. Further suitable are simethicones, which are mixtures of dimethicones with an average chain length of 200 to 300 dimethyl siloxane units and hydrogenated silicates. A detailed survey of suitable volatile silicones can also be found in Todd et al., *Cosm. Toil.* 91, 27(1976).

Typical exemplary fats are glycerides, and as waxes natural waxes among others, can be used, such as e.g. candelilla wax, carnauba wax, Japan wax, espartogras wax, cork wax, guaruma wax, rice seed oil wax, sugar cane wax, ouricury wax, montan wax, beeswax, schellac wax, spermaceti, lanolin (wool wax), bücrzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, amino acids, ceramides, pseudoceramides, essential oils, extracts of plants and vitamin complexes.

As swelling agents for aqueous phases montmorillonite, clay mineral substances, pemulen, as well as alkylmodified Carbopol types (Goodrich) can be used. Further suitable polymers or swelling agents can be found in the survey of R. Lochhead in *Cosm. Toil.* 108, 95 (1993).

UV light protection factors are e.g organic substances (light protection filters) which at room temperature are in liquid or crystalline form, and which are capable of absorbing ultraviolet radiation and to set free the received energy in the form of radiation with long wavelength, e.g. in the form of heat. UVB filters can be soluble in oils or in water. As oil soluble substances the following are mentioned as examples:

3-Benzyliden camphor, respectively 3-benzylidene norcamphor and the derivatives thereof, e.g. 3-(4-methylbenzylidene) camphor as described in EP-B1 0693471;

4-aminobenzoic acid derivatives, preferably 4-(dimethylamino) benzoic acid 2-ethylhexyl ester, 4-(dimethylamino) benzoic acid 2-octyl ester and 4-(dimethylamino) benzoic acid amyl ester;

esters of cinnamonic acid, preferably 4-methoxy cinnamonic acid 2-ethylhexyl ester, 4-methoxy cinnamonic acid propyl ester, 4-methoxy cinnamonic acid isoamyl ester, 2-cyano-3,3-phenyl cinnamonic acid 2-ethythexylester (octocrylene);

esters of salicylic acid, preferably salicylic acid 2-ethylhexylester, salicylic acid 4-isopropyl benzylester, salicylic acid homomenthylester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino-(p-carbo-2'-ethyl-1'-hexyloxy)-1,3,5-triazine and octyltriazone, as described in EP A1 0818450;

propane-1,3-diones, such as e.g. 1-(4-tert.-butylphenyl)-3-(4'-methoxy -phenyl)-propane-1,3-dion;

ketotricyclo(5,2,1,0)-decane derivatives, as described in EP-B1 0694521. As water soluble substances the following can be mentioned:

2-Phenylbenzimidazol-5-sulphonic acid and the alkali, alkaline earth, ammonium, alkylammonium, alkanolammonium and glucammonium salts;

sulphonic acid derivatives of benzophenones, preferably 2-hydroxy-4-methoxybenzophenon-5-sulphonic acid and their salts;

sulphonic acid derivatives of 3-benzyliden camphor, such as e.g. 4-(2-oxo-3-bornylidenemethyl)-benzene sulphonic acid and 2-methyl-5-(2-oxo-bornylidene) sulphonic acid and their salts.

As typical UV-A filters especially derivatives of benzoyl methane come in question, such as e.g. 1-(4'-tert.-butylphenyl)-3-(4'-methoxyphenyl)propane-1,3-dion, 4-tert.butyl-4'-methoxydibenzoyl-methane (Parsol 1789), or 1-phenyl-3-(4'-isopropylphenyl-propane-1,3-dion. The UV-A and UV-B filters can of course also be used in mixtures. In this case combinations of octocrylene or camphor derivatives with butyl methoxydibenzoyl methane are especially photosensitive.

In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (talk), barium sulphate or zinc stearate can be used. The oxides and salts are used in the form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. In sun protecting agents preferably so-called micro or nano pigments are used. Preferably micronized zinc oxide is used. Further suitable UV light protection factors can be found in the survey by P. Finkel in SÖFW-Journal 122, 543 (1996).

In addition to the primary light protection substances also secondary light protection substances of the antioxidant type find use, which interrupt the photochemichal reaction chain, which is initiated when UV radiation penetrates the skin. Typical examples of such are amino acids (e.g. glycine, histidin, tyrosin, tryptophan) and their derivatives, imidazoles (e.g. urocaninic acid) and their derivatives, peptides such as D,L-camosine, D-camosine, L-camosine and their derivatives (e.g. anserine), carotinoides, carotine (e.g. α-carotin, β-carotin, lycopin) and their derivatives, chlorogenic acid and its derivatives, liponic acid and its derivatives (e.g. dihydroliponic acid), aurothioglucose, propylthiouracil and other thiols (e.g. thioredoxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to μmol/kg), further (metal) chelating agents (e.g. α-hydroxy fatty acids, palmitic acid, phytinic acid, lactoferrine), α-hydroxy acids (e.g. citric acid, lactic acid, malic acid), humin acid, bile acid, bile extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, carnosine, butylhydroxy toluene, butylhydroxy anisol, nordihydro guajak resin acid, nordihydro guajaret acid, trihydroxy butyrophenon, uric acid and their derivatives, mannose and its derivatives, super oxide dismutase, zinc and its derivatives (e.g. ZnO, ZnSO$_4$), selen and its derivatives (e.g. selenmethionin), stilbenes and their derivatives (e.g. stilbene oxide, trans-stilbene oxide), and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. The polyols can further contain additional functional groups, especially amino groups, or be modified with nitrogen. Typical examples are:

Glycerol;

alkylene glycols, such as for example ethylene glycol, diethylene glycol, propylene glycol, butylene glycol, hexylene glycol as well as polyethylene glycols with an average molecular weight from 100 to 1000 Daltons;

oligoglycerol mixtures of technical quality with a self-condensation degree of 1.5 to 10, such as e.g. technical quality diglycerol mixtures with a diglycerol content of 40 to 50% by weight;

methyol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

amino sugarss, such as for example glucamine;

dialcoholamines, such as diethanolamine or 2-amino-1,3-propanediol.

As preservatives for example phenoxyethanol, formaldehyde solution, parabene, pentanediol or sorbic acid as well as those mentioned in enclosure 6, parts A and B of the cosmetic regulation, are further classes of substances.

As perfume oils mixtures of natural and synthetic scent substances should be mentioned. Natural odour substances are extracts of flowers (lilies, lavendel, roses, jasmin, neroli, ylang—ylang), stems and blades (geranium, patchouli, petitgrain), fruits (anis, coriander, caraway, juniper), fruit shells (bergamot, lemon, orange), roots (macis, angelica, celery, kardamon, *costus*, iris, calmus), wood (stone pine, sandel, guajac, cedar, rosewood), herbs and grass (tarragon, lemongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzyl carbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, α-isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiveri oil, oliban oil, galbanum oil, labolanum oil and lavandin oil. Preferably used are bergamot oil, dihydromyrcenol, lilial, lyral, citronellol, phenylethyl alcohol, α-hexylcinnamon aldehyde, geraniol, benzyl acetone, cyclamen aldehyde, linalool, boisambrene forte, ambroxane, indol, hedione, sandelice, lemon oil, mandarin oil, orange oil, allylamyl glycolate, cyclovertal, lavandine oil, muskateller sage oil, β-damascone, geranium oil bourbon, cyclohexyl salicylate, Vertofix coeur, iso-E-super, Fixolide NP, Evernyl, iraideini gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication *"Kosmetische Färbemittel" (cosmetic dyes) of the "Farbstoffkommission der Deutschen Forschungsgemeinschaft"*, published by Verlag Chemie, Weinheim, 1984, p. 81–106. These dyes are generally used in concentrations from 0.001 to 0.1% by weight, based on the whole mixture.

The full amount of auxiliary and additional agents can be 95 to 99.9, preferably 99 to 99.5% by weight, based on the agents.

EXAMPLES

The following table contains a number of formulation examples for different decorative cosmetic products where betaglucan is used (Highcareen® GS, Henkel KGaA, Düsseldorf/FRG). All specifications should be understood as % by weight. The formulations are as follow: (1) toned day creme; (2) powder creme; (3) pressed face powder, (4) loose face powder, (5) rouge; (6) lip gloss; (7) nurturing lip stickt; (8) decorative lip stickt; (9) eye liner, (10) mascara; (11) pressed lid shade; (12) lid shades in emulsion form; (13) pearl laquer (14) creme laquer.

TABLE 1

Example Formulation - Decorative Cosmetics

| Composition | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Glyceryl stearate | 4.0 | 1.8 | — | — | — | — | — | — | — | 6.0 | — | 5.5 | — | — |
| PEG-20 sorbityl laurate | 1.0 | 0.7 | — | — | — | — | — | | | | | | | |
| Cety alcohol | 1.0 | — | — | — | — | — | — | | | | | | | |
| Lanolinyl alcohol | — | 4.0 | — | — | 3.0 | 45.0 | 3.0 | | | | | | | |
| Lanoleyl alcohol | | | | | | | | — | — | — | 0.5 | 1.5 | — | — |
| Oleth.-10 | | | | | | | | — | — | — | — | 1.5 | — | — |
| Stearic acid | 2.0 | — | — | — | — | — | — | — | — | 1.0 | — | 1.0 | — | — |
| Paraffin oil | 4.5 | 7.5 | 2.0 | — | 2.5 | — | — | 2.0 | — | 49.0 | 3.5 | 3.0 | — | — |
| Isopropyl stearate | — | — | 2.0 | — | — | — | — | — | — | — | 2.0 | 3.0 | — | — |
| Isostearyl isostearate | | | | | | | | 12.0 | — | — | — | — | — | — |
| Myristyl lactate | | | | | | | | 6.0 | — | — | — | — | — | — |
| Cetyl stearyl octanoate | 5.0 | — | — | — | — | — | — | | | | | | | |
| Octyl palmitate | 3.0 | — | — | — | — | — | — | | | | | | | |
| Oleyl oleate | — | 3.2 | — | — | — | — | — | | | | | | | |
| Dimethyl polysiloxane | — | — | — | — | 2.5 | 10.0 | — | — | — | — | — | 2.0 | — | — |
| Stearoxy dimeticone | — | — | — | — | — | — | 1.0 | | | | | | | |
| Beeswax | — | — | — | — | — | 2.0 | — | 3.0 | — | 16.0 | — | 2.5 | — | — |
| Carnauba wax | — | — | — | — | — | 1.0 | 3.0 | 2.5 | — | 3.0 | — | — | — | — |
| Candelilla wax | — | — | — | — | — | — | 7.0 | 2.0 | — | — | — | — | — | — |
| Ozokerite | — | — | — | — | — | 2.0 | — | 2.0 | — | — | — | — | — | — |
| Ricinus oil | — | — | — | — | — | 15.0 | 82.5 | 44.5 | — | 1.5 | — | — | — | — |
| Lanolin | — | — | — | — | — | 5.0 | 10.0 | 5.0 | — | — | — | — | — | — |
| Betaglucan | 0.5 | 0.5 | 0.5 | 0.5 | 0.5 | 0.5 | 0.5 | 0.5 | 0.5 | 0.5 | 0.5 | 0.5 | 0.5 | 0.5 |
| Tocopherol acetate | — | — | — | — | — | — | 2.0 | 0.1 | — | — | — | — | — | — |
| PVP/hexadecene copolymer | | | | | | | | — | — | 3.0 | — | — | — | — |
| Polyvinyl pyrrolidone | | | | | | | | — | — | — | 0.5 | — | — | — |
| D-Phantanol | — | — | — | — | — | — | 0.5 | | | | | | | |
| Xanthan gum | 0.4 | — | — | — | — | — | — | | | | | | | |
| Magnesium stearate | — | — | 3.0 | — | — | — | — | | | | | | | |
| Zinc stearate | — | — | — | — | 4.5 | — | — | — | — | — | 2.0 | — | — | — |
| Carboxymethyl cellulose | — | 0.3 | — | — | — | — | — | — | 1.5 | — | — | — | — | — |
| Polybutylene | — | — | — | — | — | 17.0 | — | | | | | | | |
| Talcum | 4.0 | 9.0 | 30.0 | 65.5 | 17.5 | — | — | — | — | — | 36.0 | — | — | — |
| Kaolin | — | — | — | 5.0 | — | — | — | — | — | — | 5.0 | — | — | — |
| Magnesium silicate | 5.0 | 0.3 | 33.0 | 15.0 | 22.0 | — | — | — | 1.5 | — | — | 2.0 | — | — |
| Stearalkonium hectorite | | | | | | | | — | — | — | — | — | 1.0 | 10 |
| Titanium dioxide | 1.5 | 4.0 | 5.0 | — | 8.0 | — | — | 2.0 | — | — | 5.0 | 2.0 | 0.6 | 1.0 |
| Iron oxide | 0.8 | 1.1 | 2.0 | 0.5 | 4.0 | — | — | | | | | | | |
| Mica pigments | — | — | 7.0 | 11.0 | 35.0 | 3.0 | — | 6.0 | — | — | 10.0 | 8.0 | — | — |
| Bismuth oxide | | | | | | | | — | — | — | 20.0 | — | 0.2 | — |
| Triethanolamine-shellac | | | | | | | | — | 2.0 | — | — | — | — | — |
| Organic colour pigments | | | | | | | | 12.0 | 7.0 | 12.0 | 15.0 | 8.0 | 1.2 | 1.0 |
| Methyl acetate | | | | | | | | — | — | — | — | — | 8.0 | 10.0 |
| Ethyl acetate | | | | | | | | — | — | — | — | — | 8.0 | 18.0 |

TABLE 1-continued

Example Formulation - Decorative Cosmetics

| Composition | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Propyl acetate | | | | | | | | — | — | — | — | — | 12.0 | 16.0 |
| Butyl acetate | | | | | | | | | — | — | — | — | 25.0 | 23.0 |
| Polyester resin | | | | | | | | | — | — | — | — | 7.5 | — |
| Nitro cellulose/isopropanol | | | | | | | | | — | — | — | — | 21.0 | 19.0 |
| Tolusulfonamide/formaldehyde resin | | | | | | | | | — | — | — | — | 9.0 | 11.0 |
| Polyacrylate | | | | | | | | | — | — | — | — | — | 1.5 |
| Camphor | | | | | | | | | — | — | — | — | 1.5 | 1.5 |
| Dibutyl phthalate | | | | | | | | | — | — | — | — | 5.0 | 5.0 |
| Propylene glycol | 5.0 | 10.0 | — | — | — | — | — | — | 5.0 | 2.0 | — | 5.0 | — | — |
| Triethanolamine | — | 1.0 | — | — | — | — | — | | | | | | | |
| Perfume oil | 0.5 | 0.4 | 0.5 | 1.0 | 0.5 | — | 0.4 | 0.4 | — | — | — | 0.5 | — | — |
| Water | | | | | | | ad 100 | | | | | | | |

What is claimed is:

1. A decorative cosmetic preparation comprising a water-soluble β(1–3)-glucan having side chains wherein the side chains exclusively show β-(1,3) linkages as well as additional auxiliary substances and additives.

2. The decorative cosmetic preparation of claim 1 wherein said water-soluble β-glucan is comprised in said preparations in amounts of 0.1 to 5% by weight, based on the total amount of agents in said preparation.

3. The decorative cosmetic preparation of claim 1 wherein said glucans are obtained from yeasts of the family *Saccharomyces*.

4. The decorative cosmetic preparations of claim 1 wherein said additional auxiliaries and additives are members of the groups comprising oil bodies, emulsifiers, hyperfatting agents, consistency substances, thickening agents, polymers, silicone compounds, fats, waxes, stabilizing agents, biogenic active substances, deodorants, swelling agents, UV light protection agents, antioxidants, organic and inorganic colour pigments, hydrotropes, preservatives, solubilizing agents, perfume oils, colouring agents and other auxiliaries and agents which are typically part of such preparations.

5. A method of producing decorative cosmetic preparations comprising adding a water soluble β-glucan comprising a main chain of β-(1,3)-linked glucose molecules and side-chains being linked to said main chain by β-(1,6) linkages, and where said side chains comprise β-(1,3) linked glucose molecules, to additional auxiliary substances and additives.

6. The method according to claim 5 wherein said water-soluble β-glucan is comprised in said preparations in amounts of 0.1 to 5% by weight, based on the total amount of auxiliary substances and additions in said preparations.

7. A method of treating wrinkles in the skin comprising applying to the skin a preparation comprising a water soluble β(1–3) glucan having side chains wherein the side chains exclusively show (1–3) linkages.

8. The method according to claim 7 wherein the preparation contains additional auxiliary substances and additives.

9. The method according to claim 7 wherein the preparation comprises said water soluble glucan in amounts of 0.1 to 5% by weight based on the weight of the preparation.

10. A method of maintaining moisture in the skin comprising applying to the skin a preparation comprising applying to the skin a water soluble β(1–3) glucan wherein the side chains exclusively show (1–3) linkages.

11. The method according to claim 10 wherein the preparation contains additional auxiliary substances and additives.

12. The method according to claim 10 wherein the preparation comprises said water soluble glucan in amounts of 0.1 to 5% by weight based on the weight of the preparations.

* * * * *